United States Patent [19]

Malpass

[11] 4,325,840
[45] Apr. 20, 1982

[54] ORGANOMAGNESIUM COMPLEXES

[75] Inventor: Dennis B. Malpass, LaPorte, Tex.

[73] Assignee: Texas Alkyls, Inc., Deer Park, Tex.

[21] Appl. No.: 99,225

[22] Filed: Nov. 30, 1979

Related U.S. Application Data

[63] Continuation of Ser. No. 915,083, Jun. 12, 1978, Pat. No. 4,231,896, which is a continuation of Ser. No. 697,085, Jun. 16, 1976, abandoned, which is a continuation of Ser. No. 570,685, Apr. 23, 1975, abandoned.

[51] Int. Cl.$^3$ ............................................. B01J 31/12
[52] U.S. Cl. .............................. 252/431 R; 260/429.9; 260/665 R; 252/429 B; 252/429 C; 568/6
[58] Field of Search ............... 252/431 R; 260/665 G, 260/429.9, 606.5 B

[56] References Cited

U.S. PATENT DOCUMENTS

| | | | |
|---|---|---|---|
| 3,264,360 | 8/1966 | Nudenberg et al. | 252/431 R X |
| 3,444,102 | 5/1969 | Ito et al. | 252/431 R X |
| 3,737,393 | 6/1973 | de Vries | 252/431 R |
| 3,989,878 | 11/1976 | Aishima et al. | 252/431 R X |
| 4,133,824 | 1/1979 | Malpass et al. | 252/431 R X |
| 4,189,553 | 2/1980 | Birkelbach | 252/431 R X |
| 4,213,880 | 7/1980 | Knight et al. | 252/431 R |

*Primary Examiner*—Patrick Garvin
*Attorney, Agent, or Firm*—Michael J. Bradley

[57] ABSTRACT

Organomagnesium complexes, which have the formula:

$$(R'_2Mg)_m \cdot (RM)_n$$

wherein RM is an organozinc or organoboron compound, R' is a primary alkyl or aryl group, and having an m:n ratio of about 1 or greater, are disclosed. These complexes are prepared by reacting magnesium with an organohalide selected from primary alkyl halides or aryl halides in the presence of a hydrocarbon solvent and subsequently adding an organozinc or organoboron compound. Alternately, the organozinc or organoboron compound can be generated in situ by adding a zinc or boron salt which is alkylated by the magnesium alkyl. The organozinc and organoboron compounds function as solubilizing agents for organomagnesium compounds which are normally only slightly soluble or insoluble in hydrocarbon media. These complexes are characterized by very low halide content, lack of ether contamination, magnesium to metal ratios of from about 1:1 to about 20:1, and hydrocarbon solubility. Even higher ratios are conceivably obtainable. The complexes are useful as co-catalysts in combination with conventional Zeigler catalysts for polymerizing olefins, diolefins and olefin oxides, and as a source of ether-free diorganomagnesium compounds.

13 Claims, No Drawings

ORGANOMAGNESIUM COMPLEXES

This is a continuation of application Ser. No. 915,083, filed June 12, 1978, and now U.S. Pat. No. 4,231,896 which is a continuation of application Ser. No. 697,085, filed June 16, 1976, now abandoned, which in turn is a continuation of application Ser. No. 570,685, filed Apr. 23, 1975, now abandoned.

BACKGROUND OF THE INVENTION

Dialkylmagnesium compounds are well known in the art. However, the production of soluble dialkylmagnesium compounds, free of solvation and chloride, by the direct reaction of magnesium with a halide, has heretofore been unsuccessful except in very specific systems. Thus, Glaze and Selman, *Journal of Organometallic Chemistry*, volume 5, page 477 (1967), produced soluble di-n-amylmagnesium by reaction of powdered magnesium metal with n-amyl chloride and then refluxing the product with benzene. W. N. Smith, Jr. (*J. Organometal Chem.*, 64, 25 (1974) investigated the direct reaction of alkyl halides, especially long chain n-alkyl halides, with magnesium in the absence of organic bases. The resultant products, however, often showed limited solubility and/or high residual halogen content. These methods, however are imapplicable to other dialkylmagnesium compounds, particularly n-butyl or lower primary alkyl-magnesium compounds, due to their high degree of insolubility. In fact, Kamienski and Eastham, in the *Journal of Organic Chemistry*, volume 34, page 1116 (1968), found it impossible to prepare di-sec-butylmagnesium by the Glaze and Selman method. They were able to prepare di-sec-butyl chloride in the presence of an ether catalys, but the resultant product contained soluble chloride. These same authors were able to prepare hydrocarbon solutions of di-sec-butylmagnesium by an exchange process employing an activated form of magnesium chloride and sec-butyllithium in hydrocarbon media. However, this synthetic technique is not applicable to most magnesium alkyls, since these compounds are generally insoluble in hydrocarbon.

Various organoaluminum-organomagnesium complexes have been prepared by reaction of a trialkylaluminum compound with a desolvated (ether-free) Grignard reagent, by electrolysis of mixtures of alkali metal tetraalkylaluminates using a magnesium anode, and by the reaction of dialkylmagnesium compounds, prepared via the mercury-magnesium exchange method, with trialkylaluminum compounds. The complexes prepared by these processes have low Mg/Al ratios, in the range of 0.5 to 1.0 depending upon the stoichiometry of starting materials.

The electrolysis method requires the use of mixed $R_4AlM$ compounds (M=alkali metal) in a molten state and the preferred temperature range is 100°–125° C. See for example, U.S. Pat. No. 3,028,319. This temperature range precludes the preparation of complexes which may be easily pyrolyzed, for example, when R=isobutyl. Furthermore, complexes with Mg/Al ratios greater than 0.5 are not produced by this procedure.

The complexes 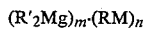 and $Me_5AlMg$ prepared by the procedure of Stucky and Atwood, *Journal of the American Chemical Society*, volume 91, page 2538 (1969), had significantly different properties than supposedly the same compound prepared earlier by Ziegler, *Annalen der Chemie*, volume 605, page 93 (1957).

The discrepancy may be due to incomplete removal of ether in the Grignard reagent used by Ziegler, since dialkylmagnesium and Grignard reagents are known to be difficult to free of complexed ethers.

Recently, hydrocarbon soluble magnesium alkylaluminum alkyl complexes were prepared by interaction of organo-aluminum compounds with the reaction product of magnesium with alkyl halides (U.S. Pat. No. 3,737,393).

It is an object of the present invention to prepare hydrocarbon soluble organomagnesium complexes, including those complexes containing the normally insoluble lower dialkylmagnesium compounds suitable for use as co-catalysts for the polymerization of olefins, diolefins, or olefin oxides.

It is another object of the present invention to prepare organomagnesium complexes wherein the Mg/M ratio is about 1 or greater. Other objects of the present invention will become apparent from the description contained below.

DETAILED DESCRIPTION OF THE DISCLOSURE

The present invention relates to organomagnesium complexes of the formula:

$$(R'_2Mg)_m \cdot (RM)_n$$

wherein RM is an organozinc or organoboron compound, R is a primary, secondary, or tertiary alkyl group, R' is a primary $C_1$ to $C_{10}$ alkyl or phenyl group, or mixture thereof, and m and n are numbers such that the ratio of m/n is about 1 or greater. In the preferred embodiment of the present invention, R is $C_1$–$C_4$ alkyl, which is either straight or branch chained, R' is methyl, ethyl, n-propyl, n-butyl, or n-amyl, and m/n is between 1 and 10. Particularly preferred in the present invention are those complexes wherein R' is a $C_1$–$C_4$ primary alkyl group.

These complexes are prepared by reacting magnesium metal with a primary alkyl halide or aryl halide in the presence of a hydrocarbon solvent and, directly thereafter, adding an organozinc or organoboron compound selected from the group consisting of dialkylzinc, alkylzinc halide, trialkylboron, dialkylboron halide or alkylboron dihalides. Alternately, the organozinc or organoboron compound may be generated in situ by alkylation of a zinc or boron salt by the organomagnesium as follows:

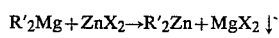

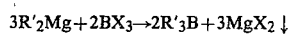

where X is a halogen, alkoxyl or carboxyl group. The resultant $R'_2Zn$ and $R'_3B$ then serves as a solubilizing agent for excess $R'_2Mg$.

After filtration of the reaction mixture, the resulting solution contains the organomagnesium complexes of the present invention and can then be diluted or concentrated as desired. The complexes can be isolated by distilling off all of the solvent to yield the viscous liquid or solid complex. However, it is preferred to handle these complexes in solution.

The organomagnesium moiety in the complexes of the present invention is generally derived from bis primary dialkyl- or diarylmagnesium compounds, obtained via the direct reaction of magnesium with a hydrocarbon halide in a hydrocarbon solvent. Although the present invention is not limited by the particular theory of the reaction mechanism, it is thought to proceed through a Grignard-type intermediate $(RMgX)_n$ which, in the absence of a solvating species, disproportionates via the Schlenk equilibrium to dialkylmagnesium and magnesium halide as follows:

$$2mR'X + 2mMg \rightarrow (R'MgX)_{2m} \rightleftarrows mR'_2Mg + mMgX_2$$

The extent of the disproportionation is dependent upon the nature of the solvent, the nature of the alkyl or aryl group, and the particular halide involved. In the present disclosure, this equilibrium is shifted completely to the right by the interaction of the organozinc or organoboron compound with the diorganomagnesium reagent to form a hydrocarbon soluble complex. Illustrative of these organomagnesium compounds are the following: dimethylmagnesium, diethylmagnesium, di-n-propylmagnesium, di-n-butylmagnesium, di-n-amylmagnesium, di-n-hexylmagnesium, diphenylmagnesium, and the like. The preferred compounds are dimethylmagnesium, diethylmagnesium, di-n-butylmagnesium and di-n-amylmagnesium. Particularly preferred are the primary alkyl magnesium compounds wherein the alkyl group is n-butyl and n-amyl.

The organozinc or organoboron compounds are generally derived from dialkylzinc, alkylzinc halides, trialkylborons, dialkylboron halides, and alkylboron dihalides. Illustrative of the organozinc compounds are the following: dimethylzinc, diethylzinc, di-n-propylzinc, diisopropylzinc, di-n-butylzinc, di-sec-butylzinc, di-tert-butylzinc, methylzinc halides, ethylzinc halides, propylzinc halides, and butylzinc halides. Preferred organozinc compounds for the complexes of the present invention are those wherein the alkyl group is from 1 to 4 carbon atoms or mixtures thereof. The alkyl group of these preferred moieties can be primary, secondary, or tertiary.

Illustrative of the organoboron compounds are the following: trimethylboron, triethylboron, triisopropylboron, tri-n-propylboron, tri-n-butylboron, tri-sec-butylboron, tri-tert-butylboron, dimethylboron halides, diethylboron halides, dipropylboron halides, dibutylboron halides, methylboron dihalides, ethylboron dihalides, propylboron dihalides, butylboron dihalides, and the like.

Illustrative of zinc salts which can be used to generate organozinc compounds in situ are the following: zinc chloride, zinc bromide, zinc iodide, zinc methoxide, zinc ethoxide, zinc isopropoxide, zinc acetate, and the like.

Illustrative of boron salts are the following: boron trifluoride, boron trichloride, boron tribromide, boron triiodide, trimethylborate, triethylborate, triisopropyl borate and the like.

With regard to the reaction of the organomagnesium with RM, the reaction appears to proceed according to the following overall lequation:

$$2mR'X + 2mMg + nRM \rightarrow (R'_2Mg)_m \cdot (RM)_n + mMgX_2$$

wherein RM is an organozinc or organoboron compound, R' is an alkyl or phenyl group or mixture thereof, X is a halide, and m and n are numbers such that the ratio of m/n is about 1 or greater.

As stated previously, the complexes of the present invention are prepared by initially reacting magnesium with a halide of the formula:

$$R'X$$

wherein R' is as defined above and X is a halogen such as chlorine or bromine, and subsequently adding an organozinc or organoboron compound directly to the reaction product.

Although magnesium turnings or shavings of commercial grade that have been further activated by milling or any other of the known methods for activating magnesium can be used in the processes herein described for the preparation of diorganomagnesium complexes, it is preferable to use magnesium powder.

The magnesium and the organic halide are normally reacted in a molar ratio of 1.2 to 1.0, i.e., a 20% molar excess of magnesium. It is understood. However, that the ratio of reactangs can be varied in the range from about 1 to 2 mols of magnesium per mole of halide and preferably in the range from about 1.1 to 1.3, i.e., a 10–30% excess magnesium. This excess magnesium is desirable to minimize coupling.

The reaction of the organohalide with magnesium can be conducted in the absence of a solvent and the product $R'_2Mg$ subsequently extracted from the solids with the organozinc or organoboron compound in a suitable solvent. The organozinc or organoboron compounds function as a solubilizing agent for the organomagnesium compounds, which are normally insoluble. However, it is preferable that the initial reaction of the magnesium with the halide be conducted in a hydrocarbon solvent followed by the addition of the organozinc or organoboron compound.

The term hydrocarbon solvent as used herein is meant to designate both aliphatic and aromatic hydrocarbons. Illustrative of the hydrocarbons which can be used in the present invention are the following: isopentane, n-hexane, n-heptane, n-octane, cyclohexane, methylcyclohexane, benzene, and toluene. Particularly preferred solvents are those aliphatic and aromatic hydrocarbons which boil between 69° and 110° C. The hydrocarbon solvent is normally employed in amounts from about 10 to 20 times the weight of magnesium charged.

The amount of organozinc or organoboron compound which is added to produce the complexes of the present invention is normally less than one mole per mole of solubilizable organomagnesium and is preferably in the molar range of from about 1:1 to about 1:20 and above, but most preferably 1:1 to about 1:10, based on a 70% yield of $R'_2Mg$. Recoveries of about 60–80% of the theoretical amount of dialkylmagnesium have been achieved. The remaining portion of the original starting materials is presumably lost to thermal decomposition and coupling.

It will be apparent to one skilled in the art that by employing the organomagnesium compound in amounts greater than 1:1 with the magnesium, organomagnesium complexes in which the Mg/M ratio is less than one can also be prepared.

Thus, in its broadest aspect, the process embodiment of the present invention encompasses the preparation of soluble organoaluminum-organomagnesium complexes of the formula:

$$(R'_2Mg)_m \cdot (RM)_n$$

wherein RM is an organozinc or organoboron compound, and n and m are numbers such that the ratio m/n is from about 0.1 to about 20 and above, and preferably from about 0.25 to about 10.

The initial reaction of the magnesium metal can be carried out at temperatures between 20° C. and 200° C. with the preferable range being between about 60° C. and 100° C. The solubilization step proceeds well at room temperature and is normally completed in 2–3 hours. However, to facilitate solubilization, it is permissible to heat the reaction mixture during the solubilization step. The upper temperature limit for this step is dependent upon the particular solubilizing compound used. Thus, if di-sec-butylzinc is used, the upper limit will be just below the decomposition temperature of di-sec-butylzinc.

It is essential to carry out the reactions of the present invention in the absence of oxygen. Thus, the manipulative steps of the process are normally carried out under an atmospheric pressure of an inert gas such as nitrogen or argon. The pressure under which the present invention is conducted is not critical and elevated pressures of several atmospheres can be employed. It has been found desirable to vigorously stir the reactant mixture during both the initial reaction of the magnesium and halide and the subsequent addition of the organozinc or organoboron compound. The reactant mixture obtained after the addition of the organozinc or organoboron compound is normally filtered and the solid washed with several portions of the hydrocarbon solvent used. The resultant wash solution can then be added to the filtrate.

It is apparent to one skilled in the art that the complexes of the present invention are a mixture of complexes having different values for m and n and that the m/n value as used herein is an average value for these numbers. It is not necessary, or even desirable, to isolate individual complexes, however, since the mixtures work just as well as the individual complexes. Furthermore, it is recognized that a certain degree of alkyl group transfer occurs between the zinc or boron and magnesium atoms of the complex. Thus, the formulae given for the complexes of the present invention are empirical rather than exact.

The complexes of the present invention are characterized by a high Mg/M ratio. They are further characterized by their freedom from undesirable contamination by halides. Furthermore, since the method of forming the complexes of the present invention does not require the use of an ether catalyst, the final product is completely ether-free.

Those compounds of the present invention which have sufficiently high Mg/M ratios (m/n of 4 or greater) can be useful in situations where diorganomagnesium reagents are desired, i.e., the complexes can be used to stimulate the "pure" organomagnesium reagent in reactivity, since they can contain 80 mole percent or greater $R'_2Mg$. In this regard, the complexes of the present invention have the substantial advantage in that they are highly soluble in hydrocarbon solvents, whereas the pure diorganomagnesium reagents are, in general, insoluble. Since these complexes are completely free of ether contamination, they can be used as Ziegler-type catalysts without catalyst poisoning which may result from the ether contamination. Organomagnesium compounds are effective catalysts for the polymerization of ethylene or propylene in the presence of titanium tetrachloride and, for the polymerization of 1,3-butadiene or 2-methyl-1,3-butadiene in the presence of titanium tetraiodide.

The present invention will be further illustrated by the following examples.

EXAMPLE 1

To a 300 milliliter three-neck flask equipped with a magnetic stirrer, reflux condenser, and addition funnel were added 5.84 grams (0.24 gram-atom) of magnesium powder 1.7 g n-butyl chloride and a few crystals of iodine. All equipment was previously flushed while hot with dry nitrogen and all reactions and manipulations carried out under a nitrogen blanket. The mixture was heated to ca 70° C. and reaction initiated. Then benzene (80 ml) was charged to reaction mixture and a solution consisting of 16.8 g n-butyl chloride in 26.6 g benzene was charged to the addition funnel. The mixture was heated to reflux and the BuCl-benzene added over a 1.5 hour period. During this period the reaction mixture assumed a muddy consistency. The mixture was refluxed about ½ hour after the addition of the n-butyl chloride solution was complete. A weight of 3.1 grams (0.025 mole) of diethylzinc was added to the mixture. After 3 hours of stirring at 82°–84° C. the mixture was filtered and the solids washed with several portions of benzene which were then added to the filtrate. Analysis of the filtrate (204.4 g) showed it to contain 0.96% Mg (or a 5.5% solution of n-Bu$_2$Mg) and 0.62% (or 1.2% solution of Et$_2$Zn) and nil chloride. The Mg/Zn ratio in the complex was 4.19 and the amount of di-n-butylmagnesium solubilized was 81%.

EXAMPLE 2

The same apparatus and procedure as in Example 1 were employed except the reactants were 27.8 grams (0.20 mole) of n-butyl bromide and 2.6 grams (0.21 mole) of diethylzinc. Analysis of the reaction supernatant showed a Mg/Zn ratio of 4.70 and the amount of di-n-butylmagnesium solubilized as complex was estimated to be 75%.

EXAMPLE 3

The same apparatus and procedure as above were employed except that 81.2 grams (0.20 mole) of n-butyl chloride and 2.7 grams (0.028 mole) of triethylboron were used as reactants. The amount of di-n-butylmagnesium solubilized was 65% of theory.

EXAMPLE 4

To a three liter four-neck flask equipped with a magnetic stirrer, reflux condenser, and addition funnel were added 20.2 grams (0.83 gram-atom) of magnesium powder and 5.7 g n-butyl chloride. The mixture was heated to ca 70° C. and reaction initiated. Then, hexane (900 ml) was charged to the reaction mixture and 58.7 g of n-butyl chloride was charged to the addition funnel.

The mixture was heated to reflux and the BuCl added over a one hour period. During this period the reaction mixture assumed a muddy consistency. The mixture was refluxed about two hours after the addition of the n-butyl chloride was complete. The reaction mixture was cooled by adding 809 mls of hexane, then a weight of 5.6 grams (0.045 mole) of diethylzinc was added to the mixture. After 2 hours of stirring at 66°–69° C. the mixture was filtered. The filtrate was concentrated by distillation of about ½ of the hexane under reduced pressure. Analysis of the filtrate (655.0 g) showed it to contain 1.04% Mg (or a 5.9% solution of n-Bu$_2$Mg) and 0.38% Zn (or 0.72% solution of Et$_2$Zn). The Mg/Zn ratio in the complex was 7.23 and the amount of di-n-butyl-magnesium solubilized was 80%.

EXAMPLE 5

To a five liter four-neck flask equipped with a magnetic stirrer, reflux condenser, and addition funnel were added 55.0 grams (2.26 gram-atom) of magnesium powder, 9.0 g n-butyl chloride and a few crystals of iodine. The mixture was heated to ca 50° C. and reaction initiated. Then hexane (2600 ml) was charged to the reaction mixture and 173.9 g of n-butyl chloride was charged to the addition funnel. The mixture was heated to reflux and the BuCl added over a 1.5 hour period. The mixture was refluxed about ½ hour after the addition of the n-butyl chloride was complete. A weight of 14.8 grams (0.120 mole) of diethylzinc was added to the mixture. After 2 hours of stirring at 50°–70° C. the mixture was filtered. Analysis of the filtrate (1452.6 g) showed it to contain 1.12% Mg (or a 6.4% solution of n-Bu$_2$Mg) and 0.40% Zn (or 0.76% solution of Et$_2$Zn). The Mg/Zn ratio in the complex was 7.40 and the amount of di-n-butylmagnesium solubilized was 67%.

EXAMPLE 6

To a three liter four-neck flask equipped with a magnetic stirrer, reflux condenser, and addition funnel were added 21.6 grams (0.89 gram-atom) of magnesium powder and 5.3 g n-butyl chloride. The mixture was heated to ca 70° C. and reaction initiated. Then hexane (1250 ml) was charged to the reaction mixture and 59.9 g of n-butyl chloride was charged to the addition funnel. The mixture was heated to reflux and the BuCl added over a 40 minute period. The mixture was refluxed about 2½ hours after the addition of the n-butyl chloride was complete. The reaction mixture was cooled by adding 155 mls of hexane, than a weight of 4.7 grams (0.048 mole) of triethylboron was added to the mixture. After 1½ hours of stirring at 66°–69° C. the mixture was filtered. The filtrate was concentrated by distillation of about ½ of the hexane under reduced pressure. Analysis of the filtrate (619.8 g) showed to contain 1.00% Mg (or a 5.7% solution of n-Bu$_2$Mg). The Mg/B ratio in the complex was estimated to be 6.6 and the amount of di-n-butylmagnesium solubilized was 72%.

what is claimed is:

1. A hydrocarbon soluble organomagnesium complex having the formula $$(R'_2Mg)_m \cdot (RM)_n$$

wherein RM is an organozinc compound selected from the group consisting of dialkylzincs, alkylzinc halides, or mixtures thereof, the alkyl portion of which R represents a primary, secondary or tertiary alkyl group, R' is selected from the group consisting of primary alkyl containing from 1 to 10 carbon atoms, and phenyl and mixtures thereof, and m and n are numbers such that the ratio of m/n is from 1 to 20.

2. The complex of claim 1 wherein the ratio of m/n is from about 1 to about 10.

3. The complex of claim 1 wherein R' is selected from the group consisting of methyl, ethyl, n-propyl, n-butyl, and n-amyl.

4. The complex of claim 1 where R is selected from C$_1$–C$_4$ alkyl.

5. An organomagnesium complex solution comprising:
   (a) hydrocarbon solvent and dissolved therein
   (b) a complex having the formula:

$$(R'_2Mg)_m \cdot (RM)_n$$

wherein RM is an organozinc compound selected from the group consisting of dialkylzincs, alkylzinc halides, or mixtures thereof, the alkyl portion of which R represents a primary, secondary or tertiary alkyl group, R' is selected from the group consisting of primary alkyl containing from 1 to 10 carbon atoms, and phenyl and mixtures thereof, and m and n are numbers such that the ratio of m/n is from 1 to 20.

6. The complex of claim 3 wherein R is selected from the group consisting of C$_1$–C$_4$ alkyl, and R is selected from the group consisting of methyl, ethyl, n-propyl, n-butyl and n-amyl.

7. The complex of claim 6 wherein the hydrocarbon is selected from the group consisting of cyclohexane, n-hexane, n-heptane and benzene.

8. The complex of claim 1 wherein R' is n-butyl.

9. The complex of claim 1 wherein R' is n-butyl and RM is diethyl zinc.

10. The complex of claim 1 wherein R' is n-butyl and RM is di-isobutyl zinc.

11. The solution of claim 5 wherein R' is n-butyl.

12. The solution of claim 5 wherein R' is n-butyl and RM is diethyl zinc.

13. The solution of claim 5 wherein R' is n-butyl and RM is di-isobutyl zinc.

* * * * *

UNITED STATES PATENT AND TRADEMARK OFFICE
CERTIFICATE OF CORRECTION

PATENT NO. : 4,325,840
DATED : April 20, 1982
INVENTOR(S) : Dennis B. Malpass

It is certified that error appears in the above-identified patent and that said Letters Patent is hereby corrected as shown below:

Column 8, claim 7, should be deleted to appear as shown below:

7. The complex of claim 6 wherein the hydrocarbon solvent is selected from the group consisting of cyclohexane, n-hexane, n-heptane and benzene.

Signed and Sealed this

Twenty-fifth Day of December 1984

[SEAL]

Attest:

Attesting Officer

GERALD J. MOSSINGHOFF

Commissioner of Patents and Trademarks